United States Patent
Wu et al.

(10) Patent No.: US 12,220,475 B2
(45) Date of Patent: Feb. 11, 2025

(54) PECTIN BASED FIRMING SYSTEM FOR ANTIAGING SKIN CARE AND MAKEUPS

(71) Applicant: L'OREAL, Paris (FR)

(72) Inventors: Chunwei Wu, Green Brook, NJ (US); Hy Bui, Piscataway, NJ (US); Zhengzheng Liao, Cranford, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 18/146,787

(22) Filed: Dec. 27, 2022

(65) Prior Publication Data

US 2024/0207164 A1 Jun. 27, 2024

(51) Int. Cl.
| | |
|---|---|
| A61K 8/73 | (2006.01) |
| A61K 8/02 | (2006.01) |
| A61K 8/06 | (2006.01) |
| A61K 8/25 | (2006.01) |
| A61K 8/34 | (2006.01) |
| A61K 8/60 | (2006.01) |
| A61K 8/81 | (2006.01) |
| A61K 8/92 | (2006.01) |
| A61Q 19/08 | (2006.01) |

(52) U.S. Cl.
CPC ............... *A61K 8/73* (2013.01); *A61K 8/025* (2013.01); *A61K 8/062* (2013.01); *A61K 8/25* (2013.01); *A61K 8/345* (2013.01); *A61K 8/60* (2013.01); *A61K 8/602* (2013.01); *A61K 8/8188* (2013.01); *A61K 8/922* (2013.01); *A61Q 19/08* (2013.01); *A61K 2800/30* (2013.01); *A61K 2800/95* (2013.01)

(58) Field of Classification Search
CPC .......... A61K 8/73; A61K 8/025; A61K 8/062; A61K 8/25; A61K 8/345; A61K 8/60; A61K 8/602; A61K 8/8188; A61K 8/922; A61K 2800/30; A61K 2800/95; A61K 8/4973; A61Q 19/08; A61Q 1/10; A61Q 1/02
See application file for complete search history.

(56) References Cited

U.S. PATENT DOCUMENTS

| | | | |
|---|---|---|---|
| 2003/0220485 A1* | 11/2003 | Ni | A61K 9/5063 536/2 |
| 2005/0080039 A1 | 4/2005 | Clark | |
| 2007/0025944 A1* | 2/2007 | Feng | A61K 8/737 424/70.13 |
| 2009/0291058 A1* | 11/2009 | Woodland | A61K 8/19 424/70.28 |
| 2014/0349902 A1 | 11/2014 | Allef et al. | |
| 2016/0206527 A1* | 7/2016 | Hueber | A61K 8/064 |
| 2017/0128407 A1* | 5/2017 | Shalviri | A61K 8/345 |
| 2017/0258203 A1* | 9/2017 | Crane | A45D 40/262 |
| 2020/0345596 A1* | 11/2020 | Montoya | A61K 8/345 |
| 2022/0054400 A1* | 2/2022 | Jamin | A61Q 19/00 |

FOREIGN PATENT DOCUMENTS

| | | |
|---|---|---|
| CN | 110420126 A | 11/2019 |
| CN | 110522659 A | 12/2019 |
| CN | 202111340582 A | 12/2021 |
| FR | 3089122 A1 | 6/2020 |
| JP | 2006241061 A | 9/2006 |
| JP | 2006241064 A | 9/2006 |

OTHER PUBLICATIONS

JJS Technical Services (Ethanol (C2H5OH), Feb. 16, 2015) (Year: 2015).*
Wurfel et al. (BioResources 2021, vol. 16, No. 4, 8457-8488) (Year: 2021).*
Procoal (Glucose, Jun. 21, 2021) (Year: 2021).*
Truth in Aging (Hydroxyethyl Acrylate/Sodium Acryloyldimethyl Taurate Copolymer, Oct. 21, 2011) (Year: 2011).*
Vityazev et al. "Pectin-silica gels as matrices for controlled drug release in gastrointestinal tract," ScienceDirect, Carbohydrate Polymers, Feb. 2017, vol. 157, p. 9-20, Elsevier.
Agoudjil et al. "Design and properties of biopolymer-silica hybrid materials: The example of pectin-based biodegradable hydrogels," Pure and Applied Chemistry, Jul. 2012, vol. 84, No. 12, p. 2521-2529.
Rangelova et al. "Synthesis and characterization of pectin/SiO2 hybrid materials," J. Sol-Gel Sci Technol, 2017, Springer Science.
Notification of Transmittal of the International Search Report and the Written Opinion of the International Searching Authority, or the Declaration issued to counterpart Application No. PCT/IB2023/063123 dated Mar. 25, 2024.
Anonymous, Mintel, "Complexion Enhancer," Jul. 30, 2007, XP093089362, Record ID No. 765089, www.gnpd.com.
Anonymous, Mintel, "The Unctuous Body Lotion," Jul. 30, 2018, Record ID No. 5842639, XP93089357.

(Continued)

*Primary Examiner* — Lezah Roberts
*Assistant Examiner* — Abdulrahman Abbas
(74) *Attorney, Agent, or Firm* — McNees Wallace & Nurick LLC

(57) ABSTRACT

A cosmetic composition includes a firming system that includes: a pectin; at least one powder; water; at least one fatty compound; and at least one plasticizer. The firming system when is spreadable and wherein upon drying the firming system forms a firming film that exhibits cohesion and adhesion when applied to a substrate. The pectin may comprise low methoxyl pectin, and the firming system may further include at least one monosaccharide, disaccharide or combination thereof. The composition may include a cosmetic carrier system wherein the firming system and cosmetic carrier system is in the form of liquidous or creamy type emulsion or an oil free serum for application to skin to ameliorate the signs of aging or a viscous liquidous emulsion or suspension for application as a makeup to keratinous tissue selected from skin, lashes and hair to confer firming to the keratinous tissue.

6 Claims, 6 Drawing Sheets

(56) References Cited

OTHER PUBLICATIONS

Anonymous, Mintel, "Midnight Lady Crush Whitening Perfume Lotion," May 1, 2019, Record ID No. 6515527, XP93089354.
Anonymous, Mintel, "Body Care Cellular Moisturisation Progressive Natural Tan Cream," May 13, 2022, Record ID No. 9564310, XP93089353.
Anonymous, Mintel, "Hydrating Awakening Veloute Normal to combination Skin," Sep. 25, 2014, Record ID No. 2588423, XP93089358.
Anonymous, Mintel, "Ingenious Cream SPF 15," Jul. 4, 2016, Record ID No. 4111447, XP93089365.
Anonymous, Mintel, "Radiance Anti-Wrinkle Night Cream," Nov. 22, 2010, Record ID No. 1445094, XP93089360.
Search Report issued to French counterpart Application No. FR 2302080 dated Oct. 11, 2023.

\* cited by examiner

MOA: Interaction between pectin and silica in the hybrid O/I film network

PECTIN BASED FIRMING SYSTEM FOR ANTIAGING SKIN CARE AND MAKEUPS

FIELD OF TECHNOLOGY

The present disclosure is directed to compositions for conferring firming and tightening properties to substrates, in particular skin and hair.

BACKGROUND

Film-forming polymers based film technology has been widely used in makeups such as mascara, nail polish and lipstick, as well as in haircare and skincare for substrate bonding, deposition and retention, and tightening efficacy. As used for applications that include anti-ageing, wrinkle smoothing and filling, reduction of puffiness, lifting and tightening, film forming polymers and technology has proven indispensable to consumers, and is primarily leveraged to offer short term and immediate perceived benefits while relying on the use of anti-ageing bioactives to obtain longer term benefits.

Film forming polymers in skin cosmetics, both water and oil-based, have long been dominated by synthetic cross-linked polymers or copolymers. Despite growing consumer expectation for natural, biodegradable and sustainable products, naturally occurring biopolymers (e.g., polysaccharides, proteins), have suffered from inherently inferior mechanical properties, and have thus not provided robust solutions for use as film forming materials in anti-aging products.

The inventors have as one objective to incorporate natural ingredients in film forming applications to address what is lacking in the art. As disclosed herein, the nature based film forming technology is applicable to skincare anti-ageing applications that can benefit facial and other skin of a consumer, and also provides a platform for use in hair care and make up applications.

BRIEF SUMMARY OF THE INVENTION

This summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

In one aspect, the present disclosure provides a cosmetic composition, comprising:
a firming system that includes:
  a pectin;
  at least one powder;
  water; and
  at least one plasticizer,
 wherein the firming system is spreadable and wherein upon drying the firming system forms a firming film that exhibits cohesion and adhesion when applied to a substrate.

In some embodiments, the pectin comprises low methoxyl pectin, and the firming system further includes at least one monosaccharide, disaccharide or combination thereof and preferably a polymeric thickener in accordance with the disclosure to provide a texture that is appreciably improved when used instead of a metal salt such as a calcium salt.

In some embodiments, the composition expressly may include at least one metal salt. In some embodiments, the composition expressly may include any one or more of metal salts selected from magnesium chloride, calcium chloride, a manganese salt of pyrrolidone carboxylic acid, manganese gluconate, manganese sulfate, manganese chloride, a copper salt of pyrrolidone carboxylic acid, copper gluconate, copper sulfate, copper chloride, a zinc salt of pyrrolidone carboxylic acid, zinc gluconate, zinc sulfate, zinc chloride, or combinations thereof.

In some embodiments, the composition expressly excludes metal salts. In some embodiments, the composition expressly excludes or essentially free from any one or more of metal salts selected from magnesium chloride, calcium chloride, a manganese salt of pyrrolidone carboxylic acid, manganese gluconate, manganese sulfate, manganese chloride, a copper salt of pyrrolidone carboxylic acid, copper gluconate, copper sulfate, copper chloride, a zinc salt of pyrrolidone carboxylic acid, zinc gluconate, zinc sulfate, zinc chloride, or combinations thereof.

In some embodiments, the low methoxyl pectin has a molecular weight from about 10 k Da to about 1000 k Da.

In some embodiments, the amount of the pectin present in the composition is at a concentration from about 0.5% to about 10.0%.

In some embodiments, the one or more powders comprises one or more of silica or silicates or combinations thereof, which may be in dry powder form prior to addition to the composition, or in liquid suspension or solution.

In some embodiments, the powder is in the form of silica particles including silica nano or microparticles, sodium silicate, potassium silicate, alumina, titanium dioxide, zinc oxide, or a combination thereof.

In some embodiments, the at least one powder is present in the composition at a concentration from about 0.1% to about 10%, by weight, based on the weight of the composition.

In some embodiments, the composition is in the form of an essentially oil free serum or gel.

In some embodiments, the composition comprises at least one fatty compound. In some embodiments, the composition is in the form of an emulsion and comprises at least one fatty compound.

In some embodiments, the fatty compound includes one or more plant butters, the one or more plant butters selected from the group consisting of *Butyrospermum parkii* (shea) butter, *Astrocaryum murumuru* Seed butter, *Theobroma cacao* (cocoa) seed butter, almond butter, aloe butter, apricot kernel butter, avocado butter, coconut cream butter, cupuacu butter, dhupu butter, hemp butter, jojoba butter, kokum butter, macadamia nut butter, mango butter and combinations thereof.

In some embodiments, the fatty compound includes one or more plant butters wherein the total amount of plant butter present in the composition at a concentration from about 2% to about 9%, by weight, based on the weight of the composition.

In some embodiments, the fatty compound includes one or more emollient oils present in the composition at a concentration from about 0.5% to about 6%, by weight, based on the weight of the composition.

In some embodiments, the fatty compound includes one or more waxes selected from the group consisting of *Copernicia cerifera* (Carnauba) wax, candelilla wax, sunflower wax and combinations thereof.

In some embodiments, the fatty compound includes one or more waxes, wherein the total amount of wax, is present in the composition at a concentration from about 0.05% to about 5%, by weight, based on the weight of the composition.

In some embodiments, the composition comprise glycerin as the plasticizer.

In some embodiments, the amount of each plasticizer, is present in the composition at a concentration from about 2% to about 10%, by weight, based on the weight of the composition.

In some embodiments, the fatty compound and plasticizer are present in a ratio of fatty compound to plasticizer of about 1:1.

In some embodiments, the composition includes at least one metal salt selected from calcium chloride, a manganese salt of pyrrolidone carboxylic acid, manganese gluconate, manganese sulfate, manganese chloride, a copper salt of pyrrolidone carboxylic acid, copper gluconate, copper sulfate, copper chloride, a zinc salt of pyrrolidone carboxylic acid, zinc gluconate, zinc sulfate, zinc chloride, or combinations thereof.

In some particular embodiments, the metal salt is calcium chloride.

In some embodiments, the amount of the at least one metal salt is present in the composition at a concentration from about 0.01% to about 1%, by weight, based on the weight of the composition.

In some embodiments, water in the composition is present from about 5% to about 75%, and the composition has a pH in a range from about 4.0 to about 8.5.

In some embodiments, the composition comprises one or more surfactants selected from sorbitan isostearate, polysorbate 60, stearic acid, cetearyl alcohol, polysorbate 20, glyceryl stearate (and) peg-100 stearate, cetearyl alcohol (and) ceteareth-20, glyceryl stearate, sorbitan stearate, or combinations thereof.

In some particular embodiments, the composition includes a blend of surfactants comprising sorbitan isostearate and polysorbate 60.

In some embodiments, the total amount of surfactant present in the composition is at a concentration from about 0.01% to about 20%, by weight, based on the weight of the composition.

In some embodiments, the composition includes at least one cosmetically acceptable polymer, wherein the at least one polymer has a glass transition ($T_g$) that is in the range from about −70° C. to about −30° C., wherein, for example, Polyethylhexylacrylate has a $T_g$ that is about −70° C., Polyurethane (polyether polyol/MDI) has a $T_g$ that is about −30° C., and a silicone has a $T_g$ that is about −90°, the polymer being present in the composition at a concentration from about 0.4% to about 3%, by weight, based on the weight of the composition.

In some particular embodiments, the composition includes hydroxyethyl acrylate/sodium acryloyldimethyl taurate copolymer.

In some embodiments, the composition is provided in liquid form, for example as a lotion or cream. In some embodiments, the composition is provided as a makeup such as a foundation or mascara.

In another aspect, the present disclosure provides a cosmetic composition, comprising:
a firming system that includes:
0.5-10% of pectin;
at least one powder comprising about 0.1 to about 10% of silica particles selected from nano particles and microparticles;
water;
at least one fatty compound comprising from about 4% to about 8% of plant butters; and
at least one plasticizer;
wherein all amounts are present by weight, based on the weight of the composition,
wherein the firming system is spreadable and wherein upon drying the firming system forms a firming film that exhibits cohesion and adhesion when applied to a substrate.

In another aspect, the present disclosure provides a cosmetic system, comprising:
an applicator; and
a firming system that includes:
pectin;
at least one powder;
water; and
at least one plasticizer; and
a cosmetic carrier system for a cosmetic product selected from the group consisting of a skin anti-aging treatment and a makeup,
wherein the firming system is spreadable and wherein upon drying the firming system forms a firming film that exhibits cohesion and adhesion when applied to a substrate.

In some embodiments, the applicator may be selected from a roller surface of a rolling applicator, a bristle surface of a brush, a sprayer, a pad, or spatula.

In some embodiments, the composition is contained within the applicator. In some embodiments, the cosmetic system comprises a container wherein the composition is separately contained from the application.

In some embodiments, the firming system and cosmetic carrier system is in the form of liquidous or creamy type emulsion or a serum for application to skin to ameliorate the signs of aging.

In some embodiments, the firming system and cosmetic carrier system is in the form of viscous liquidous emulsion or suspension for application as a makeup to keratinous tissue selected from skin, lashes and hair to confer firming to the keratinous tissue.

In some embodiments the composition further comprises at least one fatty compound.

Other features and advantages of the present invention will be apparent from the following more detailed description, taken in conjunction with the accompanying drawings which illustrate, by way of example, the principles of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

BRIEF DESCRIPTION OF THE DRAWINGS

Features and advantages of the general inventive concepts will become apparent from the following detailed description made with reference to the accompanying drawings.

Aspects and many of the attendant advantages of the claimed subject matter will become more readily appreciated as the same become better understood by reference to the following detailed description, when taken in conjunction with the accompanying drawings.

The detailed description set forth below in connection with the appended drawings, where like numerals reference like elements, is intended as a description of various embodiments of the disclosed subject matter and is not intended to represent the only embodiments. The embodiments described in this disclosure are provided merely as examples or illustrations and should not be construed as preferred or advantageous over other embodiments. The illustrative examples provided herein are not intended to be exhaustive or to limit the claimed subject matter to the exact forms disclosed.

DETAILED DESCRIPTION OF THE INVENTION

Film forming polymers in skin cosmetics, water or oil-based, have long been dominated by synthetic cross-linked polymers or copolymers. In recent years, there is rising demand in the industry for film forming products that include naturally occurring substances in a more green and sustainable way. The instant invention involves a firming system that a natural polysaccharide pectin, which is a water soluble fiber abundant in the cell walls of fruits and vegetables, particularly citrus, apple and beet.

A brand new biopolymer or polysaccharide pectin-based film forming technology has been developed by the inventors, which has demonstrated, in an exemplified skin care formulation, immediate and long lasting appearance benefits of wrinkling smoothing, de-puffiness and anti-dark circle as a result of the superb tightening and lifting effect of the film. In various embodiments, provided is a composition that includes a firming system comprising pectin, at least one powder, at least one fatty compound, a plasticizer and water.

According to the invention, the pectin is used in combination with a powder, in some particular examples selected from silica or silicates or combinations thereof, which may be in dry powder form prior to addition to the composition, or in liquid suspension or solution, including silica particles that may be micro or nano scale or silicates, or other powders selected from sodium silicate, potassium silicate, alumina, titanium dioxide, zinc oxide, or a combination thereof whereby the molecular weight and acetylation ratio of the selected pectin, in some embodiments, low methoxyl pectin, confers ready solubility in water without gelling as other polysaccharides typically do, allowing for associations between the pectin and powder in liquid state and allowing further crosslinking between the pectin and powder after film drying.

Figure 1:
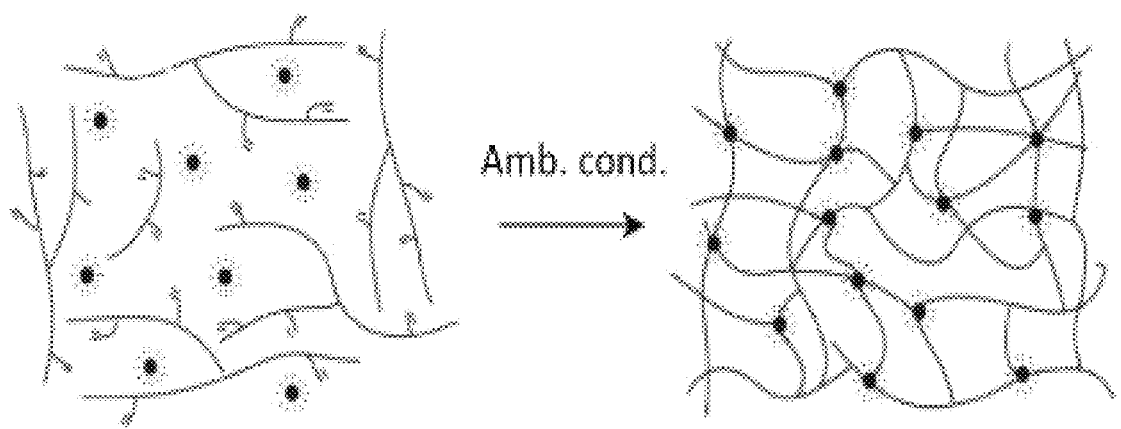
FIG. 1 demonstrates posited interaction between pectin and silica in film formation according to the disclosure.
Figure 2:
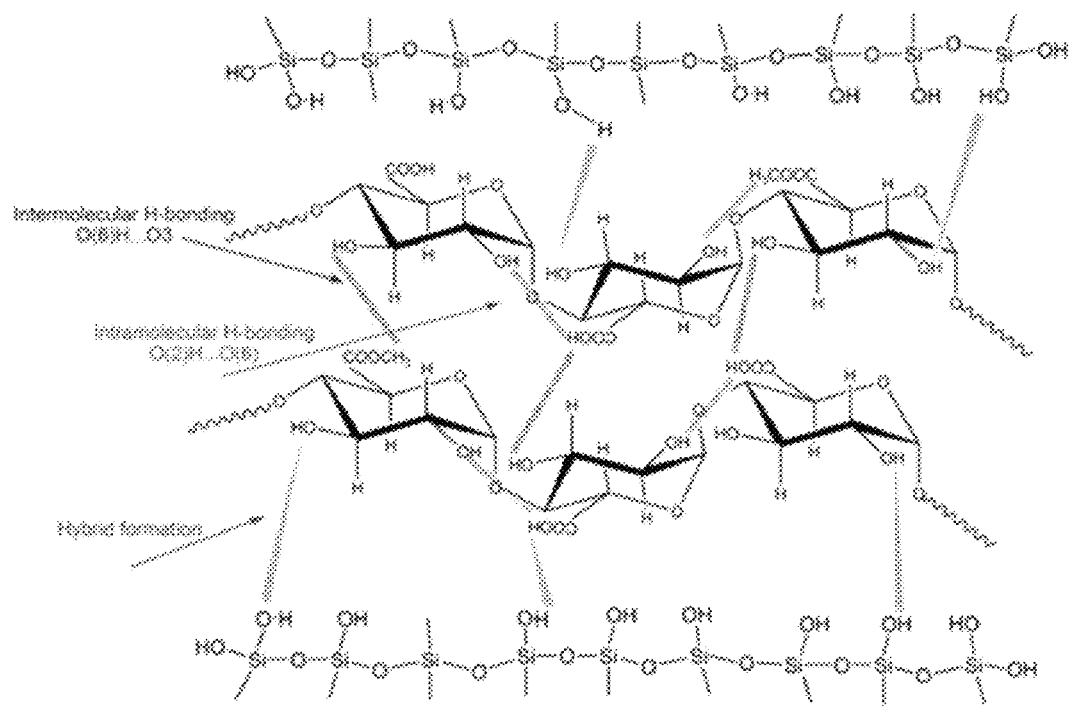
FIG. 2 demonstrates posited molecular interaction between pectin and silica to form a hybrid organic/inorganic film network.

The inventors have found that the composition including the firming system according to the disclosure unexpectedly provides a firming film in which the interaction between pectin and powder, for example, silica, is posited to form hydrogen bonds that result in a film and not a gel, wherein the film is sufficiently firm to tighten and firm a substrate such as skin and is pliable and resistant to cracking and flaking, as represented in FIG. 1 and FIG. 2. The firming system is particularly useful for firming and tightening lines and bags on skin, and thus may be used anywhere on the body where bags and lines are desired to be reduced. Exemplary embodiments have been applied to the skin around eyes to effectively eliminate lines and bags almost immediately after application and for up to at least 7 hours. The composition including the firming system is able to be readily removed using water or a cleanser.

Additional ingredients, including glycerin, emollient oils, thickening polymers, and optionally, wax, hyaluronic acid, and other actives in water based system, as employed in exemplified compositions, demonstrate superb instantly visible and long lasting tightening and firming performance to provide perceived antiaging benefits and are easily washable for removal. The key components of natural polysaccharide pectin and silica particles also exhibit moisturizing and mattifying effects.

In various embodiments which comprise at least one fatty compound, the ratio between emollient oil and glycerin affects cohesion and adhesion, elasticity and compliance of the film after drying on skin and enables balanced benefits of efficacy, user comfort and long lastingness.

Now with reference to the exemplified embodiments that include pectin use with silica or silicate, for example silica particles including silica nano or microparticles or silicates, or other powders selected from sodium silicate, potassium silicate, alumina, titanium dioxide, zinc oxide, or a combination thereof, without intending to be bound by theory, the inventors posit that using inorganic silica particles as physical cross-linker, through various inter- and intra-molecular interactions between the silanol groups (—Si—OH) on silica surface and the abundant carboxyl (—COOH), carboxylate (—COO) and hydroxyl (—OH) groups on the side chains of the linear pectin molecules create a hybrid film network that possesses both organic and inorganic attributes, contributing to superb physical and mechanical properties (adhesion, cohesion) of the resulting firming film. These posited robust inter- and intra-molecular interactions including hydrogen bonding between the linear acidic polysaccharide equipped with abundant carboxyl (—COOH), carboxylate (—COO) and hydroxyl (OH) groups and the silanol surface functional groups (—Si—OH) on silica particles (in the case of combination of pectin with silicates, silica particles are formed in situ via hydration and condensation processes after the mixing of silicates with the acidic pectin molecules), a strong hybrid organic/inorganic 3-dimensional continuous network is able to form.

The composition provides the firming system that forms in liquidous state a physical bonding between the pectin and the powder which upon drying under ambient conditions (standard ranges for humidity and pressure and temperature of about 15° C.-25° C. (59° F.-77° F.), forms a hybrid film with superb properties. The resultant film is flexible to allow for comfort, and resistant to flaking, delaminating, cracking, lifting and bubbling.

In accordance with the various embodiments, a composition including the firming system of the disclosure may be in a form including a suspension, lotion, cream, serum, gel, stick, spray, ointment, paste, foam, mousse, cream, wipe, patch, or strip. And the product may be a skin treatment or a makeup such as but not limited to a foundation or mascara.

Composition

Pectin

In accordance with the various embodiments, the composition includes pectin. In various embodiments, the pectin may be selected from low methoxyl and high methoxyl pectin, or a combination thereof. In some embodiments the pectin is low methoxyl pectin.

Pectin is a naturally-occurring polysaccharide found in many plants, and is economical, abundant in source, 100% natural, biodegradable and sustainable.

High methoxyl pectins contain more than 50% polygalacturonic acid units, while low-methoxyl pectins generally contain less than 50% polygalacturonic acid units. High methoxyl pectins are known to gel in the presence of at least 60% sugar, by weight of the combination of pectin and sugar, and at a pH of 2.6-34; low-methoxyl pectins are known to require the presence of polyvalent metal ions to gel, such as calcium, magnesium and aluminum plasma at a pH of 2-7 and low-methoxyl pectins are synergistic with Locust Bean Gum.

In accordance with the current invention, the inventors have unexpectedly prepared compositions in which the use of pectin with a polymer, for example, pectin-$SiO_2$, provides superior hydrogen bonding for film formation as compared with Ca++-pectin interaction.

In some embodiments the pectin comprises low methoxyl pectin and sucrose. In some embodiments, the low methoxyl pectin has a molecular weight from about 10 kDa to 1000 kDa.

In accordance with the various embodiments, the amount of the pectin present in the composition can range from about 0.5% to about 10.0%, or from about 1.0% to about 9.0%, or from about 2.0% to about 8.0%, or from about 3.0% to about 7.0%, or from about 5.0% to about 6.0%, or any suitable combination, sub-combination, range, or sub-range thereof by weight, based on the weight of the skin treatment system. One of ordinary skill in the art, however, will appreciate that other ranges are within the scope of the invention.

Thus, pectin, in some embodiments low-methoxyl pectin, is present, by weight, based on the total weight of the composition, or from about from about 0.50, 0.60, 0.70, 0.80, 0.90, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, to about 10.0 weight percent, including increments and ranges therein and there between.

Powder

In accordance with the disclosure, one or more powders are present in the composition.

As used herein the term "powder" means and includes materials that are in a dry powderous state, and materials that are in a liquidous suspended state or solution, such as but not limited to a sodium silicate solution.

According to the invention, the powder is selected from silica or silicates or combinations thereof, which may be in dry powder form prior to addition to the composition, or in liquid suspension or solution, including silica particles that may be micro or nano scale or silicates, or other powders selected from sodium silicate, potassium silicate, alumina, titanium dioxide, zinc oxide, or a combination thereof.

In some embodiments, the one or more powders comprises one or more of silica or silicates or combinations thereof silica or silicates or combinations thereof. In some embodiments, the powder is in the form of silica particles including silica nano or microparticles or silicates, or other powders selected from sodium silicate, potassium silicate, alumina, titanium dioxide, zinc oxide, or a combination thereof. In some particular embodiments, the powder is in the form of silica microparticles. In other particular embodiments, the powder is a silicate, such as sodium silicate, potassium silicate, or a combination thereof.

The one or more powders may be selected from silica and silicates, for example, silica microparticles, hydrated silica, silica alumina, silica silylate, silica (and) methicone, silica (and) dimethicone, sodium silicate, potassium silicate, aluminum magnesium silicate, chemically modified magnesium aluminum silicate, calcium silicate, magnesium silicate, sodium potassium aluminum silicate, strontium silicate, or combinations thereof.

In some embodiments, the one or more powders may be selected from spherical microparticles of porous silica having a mean particle size from 0.5 to 20 µm whose INCI name is silica sold by the company JCG Catalysts and Chemicals under the name Spheron L-1500.

According to some embodiments, the composition excludes hydrophobic aerogel.

Silica aerogels are porous materials obtained by replacing (by drying) the liquid component of a silica gel with air. Hydrophobic silica aerogel particles useful according to embodiments of the disclosure include silylated silica (INCI name: silica silylate) aerogel particles. The preparation of hydrophobic silica aerogel particles that have been surface-modified by silylation is described more fully in U.S. Pat. No. 7,470,725, incorporated by reference herein. In some embodiments, aerogel particles of hydrophobic silica surface-modified with trimethylsilyl groups may be chosen. For example, the aerogel sold under the name VM-2260® by the company Dow Corning, the particles of which have an average size of about 1000 microns and a specific surface area per unit of mass ranging from 600 to 800 $m^2/g$, or the aerogel sold under the name VM-2270®, also by the company Dow Corning, the particles of which have an average size ranging from 5 to 15 microns and a specific surface area per unit of mass ranging from 600 to 800 $m^2/g$, may be chosen. In some embodiments, the aerogels sold by the company Cabot under the names Aerogel TLD 201®, Aerogel OGD 201®, and Aerogel TLD 203®, CAB-O-SIL TS-530, CAB-O-SIL TS-610, CAB-O-SIL TS-720, Enova Aerogel MT 1100®, and Enova Aerogel MT 1200®, may be chosen.

The at least one powder is present in the composition at a concentration from about 0.01% to about 25%, or from about 0.05% to about 20%, or from about 0.1% to about 10%, or from about 1% to about 5.0%, or from about 2% to about 4%, or about 3%, or any suitable combination, sub-combination, range, or sub-range thereof by weight, based on the weight of the composition. One of ordinary skill in the art, however, will appreciate that other ranges are within the scope of the invention. In some embodiments, the composition includes more than one powder, each powder present in an amount as set forth herein above, wherein each different powder may be present within one of the ranges selected from the ranges set forth herein above.

Thus, each one of the at least one powder, or a combination thereof, may be present by weight, based on the total weight of the composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0 to about 25.0 percent by weight, including increments and ranges there between.

Fatty Compound

In accordance with the disclosure, one or more fatty compounds may be present in the composition. The fatty compounds include one or more of non-silicone oils of animal, plant, animal or synthetic origin, fatty alcohols, fatty acids, esters of a fatty acid and/or of a fatty alcohol, non-silicone waxes, and silicone oils.

In some embodiments, the composition includes one or more plant butters, the one or more plant butters selected from the group consisting of *Butyrospermum parkii* (shea)

butter, *Astrocaryum murumuru* Seed Butter, *Theobroma cacao* (cocoa) seed butter, almond butter, aloe butter, apricot kernel butter, avocado butter, coconut cream butter, cupuacu butter, dhupu butter, hemp butter, jojoba butter, kokum butter, macadamia nut butter, mango butter and combinations thereof.

In accordance with the various embodiments, the amount of plant butter present in the composition may be at least 1%, or from about 1% to about 15%; or, from about 2% to about 9%, or from about 2.5% to about 8%, or from about 3% to about 5%, or any suitable combination, sub-combination, range, or sub-range thereof by weight, based on the weight of the composition. One of ordinary skill in the art, however, will appreciate that other ranges are within the scope of the invention.

In some embodiments, the at least one butter has a melting point in the range of from about 30 to about 45 degrees Celsius.

Thus, any one of or a combination of plant butters may be present, by weight, based on the total weight of the moisturizing peel cream, from about 1, 2, 3, 4, 5, 6, 7, 8, 9, 10, 11, 12, 13, 14, to about 15 weight percent, including increments and ranges therein and there between.

In some embodiments, the composition includes one or more emollient oils. In accordance with the various embodiments, nonlimiting examples of emollient oils include octyldodecanol, diisopropyl adipate, isononyl isononanoate, *Limnanthes alba* (meadowfoam) seed oil, dicaprylyl carbonate, squalane, dimethicone, and behenyl alcohol.

In accordance with some embodiments, the amount of an emollient oil present in the compositions can range from about 0.5% to about 6%, or from about 0.5% to about 3%, or from about 1% to about 1.5%, or any suitable combination, sub-combination, range, or sub-range thereof by weight, based on the weight of the composition. One of ordinary skill in the art, however, will appreciate that other ranges are within the scope of the invention.

In accordance with some embodiments, the composition comprises one or more of emollient oil. In accordance with some embodiments, the amount of combined emollient oil present in the compositions can range from about 5% to about 20%, or from about 5% to about 15%, or from about 5% to about 10%, or any suitable combination, sub-combination, range, or sub-range thereof by weight, based on the weight of the composition. One of ordinary skill in the art, however, will appreciate that other ranges are within the scope of the invention.

Thus, an emollient oil in the composition may be present by weight, based on the total weight of the composition, from about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.0, 5.1, 5.2, 5.3, 5.4, 5.5, 5.6, 5.7, 5.8, 5.9, to about 6.0 percent, including increments and ranges therein and there between. And in combination, emollient oils in the composition may be present by weight, based on the total weight of the composition, from about 1, 2, 3, 4, 5, 6, 7, 8, 9, 10, 11, 12, 13, 14, 15, 16, 17, 18, 19, to about 20 percent, including increments and ranges therein and there between.

More generally, in accordance with the some embodiments, the composition includes any one or a combination of cosmetic oils. In some embodiments, the oil is generally immiscible in water.

The oil may be selected from silicones, hydrocarbons, fatty alcohols, glycols, and vegetable oils. The oil may include one or a combination of polar and non-polar oil. In some embodiments, the oil may be chosen from hydrocarbon-based oils from plants or of plant origin, mineral oil, ester oils, fatty alcohols containing from 12 to 26 carbon atoms, fatty acids containing from 12 to 26 carbon atoms and vinylpyrrolidone copolymers, and combinations thereof.

Silicone Oils

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil, or a synthetic hydrocarbon-based oil. Further, suitable oil may be a mineral hydrocarbon-based oil, a plant hydrocarbon-based oil, or a synthetic hydrocarbon-based oil.

The composition may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl (methyldiphenyl)trisiloxanes or (2-phenylethyl)trimethylsiloxysilicates.

Other examples of silicone oils that may be mentioned include volatile linear or cyclic silicone oils, especially those with a viscosity 8 centistokes (8×106 m2/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The composition may comprise one or more fluoro oils. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The composition may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the composition may include a synthetic oil selected from the group consisting of hydrogenated polyisobutene and hydrogenated polydecene. A hydrocarbon-based oil may be a non-volatile hydrocarbon-based, such as:
  (i) hydrocarbon-based oils of plant origin, such as glyceride triesters, which are generally triesters of fatty acids and of glycerol, the fatty acids of which can have varied chain lengths from C4 to C24, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ÿ 10, for instance Purcellin oil (cetearyl octanoate), isopropyl myristate, isopropyl palmitate, C12-C15 alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear C12-C13 alkyl) tartrates, such as those sold under the name Cosmacol ETI® by Enichem Augusta Industriale, and also di(linear C14-C15 alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid, or linolenic acid;

(vii) carbonates, such as dicaprylyl carbonate, such as the product sold under the name Cetiol CC™ by Cognis;

(viii) fatty amides, such as isopropyl N-lauroyl sarcosinate, such as the product sold under the trade name Eldew SL 205™ from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

Hydrocarbon-based oils may be glyceride triesters and in particular to caprylic/capric acid triglycerides, synthetic esters and in particular isononyl isononanoate, oleyl erucate, C12-C15 alkyl benzoate, 2-ethylphenyl benzoate and fatty alcohols, such as octyldodecanol. As volatile hydrocarbon-based oils, mention is made of hydrocarbon-based oils containing from 8 to 16 carbon atoms and in particular of branched C8-C16 alkanes, such as C8-C16 isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C C8-C16 esters, and isohexyl neopentanoate.

In some embodiments, the composition may comprise one or more oils such as from those described herein above, and from oils that may be selected from branched or linear, liquid alkane with carbon chain length of C11 to C20. In various embodiments, liquid alkanes may be selected from those with a carbon chain length of from C11 to C20. The liquid alkanes may be selected from those with a carbon chain length of from C11 to C20, or from C15 to C19, or one of C11, C12, C13, C14, C15, C16, C17, C18 to C19. In some embodiments, suitable liquid alkanes that may be used according to the disclosure include hydrocarbon-based oils containing from 8 to 16 carbon atoms, and especially branched C8-C16 alkanes such as C8-C16 isoalkanes.

In some embodiments, the composition may comprise one or more oils selected from polar emollients selected from esters, triglycerides, ethers, carbonates, alcohols, oils, butters, fatty acids, and their combinations thereof. In various embodiments, the polar emollients may be selected from those with a molecular weight of 400 g/mol or less. More, generally, the polar emollient may have a molecular weight in the range from about 50 g/mol % to about 350 g/mol.

In some embodiments, the composition may comprise polar emollients that include those derived from C12-C50 fatty acids, preferably C16-C22 saturated fatty acids, and monohydric alcohols. In some embodiments, such esters may be chosen from isopropyl myristate, methyl palmitate, isopropyl laurate, isopropyl palmitate, ethylhexyl palmitate, ethylhexyl laurate, ethylhexyl oleate, ethylhexyl isononanoate, myristyl myristate, 2-ethylhexyl caprate/caprylate (or octyl caprate/caprylate), 2-ethylhexyl palmitate, isostearyl neopentanoate, isononyl isononanoate, hexyl laurate, esters of lactic acid and of fatty alcohols comprising 12 or 13 carbon atoms, dicaprylyl carbonate and their mixtures.

In some embodiments, the fatty compound includes, but is not limited to: 1) C6-C19 lower alkanes, non-silicone oils of animal, plant, animal or synthetic origin, fatty alcohols, fatty acids, non-silicone waxes, and silicones; 2) hydrocarbon-based oils of animal origin, such as perhydrosqualene; 3) fluoro oils, perfluoromethycyclopentane and perfluoro-1,3-dimethylcyclohexane, sold under the name FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050@ by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the same PF 5052® by the company 3M. 4) linear or branched saturated fatty alcohols having from 6 to 30 carbon atoms or from 8 to 30 carbon atoms, for instance cetyl alcohol, stearyl alcohol, and the mixture thereof (cetyl-stearyl alcohol), octyldodecanol, 2-butyloctanol, 2-hexyldecanol, 2-undecylpentadecanol, oleyl alcohol, and linoleyl alcohol. In some particular embodiments, a composition according to the disclosure includes one or more of mineral oil, hemisqualane, dimethicone, squalane, castor oil, isohexadecane, and coconut oil.

In some embodiments, at least one fatty compound describes an organic compound that is insoluble in water at ordinary ambient temperature (25° C.) and at atmospheric pressure (760 mmHg). In some embodiments, the at least one fatty compound has a water solubility of less than 5%. In some embodiments, the at least one fatty compound has a water solubility of less than 1%. In some embodiments, the at least one fatty compound has a water solubility of less than 0.1%. Although these fatty compounds are given as an example, it will be appreciated that other compounds compatible with cosmetic applications known in the art may be used.

In some embodiments, an oil may be chosen from squalane, purcellin oil (cetostearyl octanoate), hemisqualane, isononyl isononanoate, C12 to C15 alkyl benzoate, 2-ethylhexyl palmitate, isodecyl neopentanoate, tridecyl neopentanoate, octyldodecyl neopentanoate, 2-octyldodecyl stearate, 2-octyldodecyl erucate, oleyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate and 2-diethylhexyl succinate, cocoglyceride, cyclomethicone, dimethicone, dicaprylyl carbonate, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of C9-C15 alcohols, alkanes, mineral oil, silicone, dimethyl polysiloxane, ether, polyoxypropylene butyl ether, polyoxypropylene cetyl ether, C12-C15 alkyl benzoate, aryl alkyl benzoate, Isopropyl Lauroyl sarcosinate, and any combinations thereof. In some embodiments, an oil may be chosen Isopropyl myristate, dicaprylyl ether, ethylhexyl palmitate, Isopropyl palmitate, cetearyl ethylhexanoate, Isononyl isononanoate, isopropyl isostearate, diisopropyl sebacate, coco caprylate/caprate, diisopropyl adipate, isohexadecane, C15-19 alkane, isododecane, undecane, tridecane, dodecane, and combinations thereof. In some embodiments, silicone oils, synthetic and petroleum based oils, and combinations thereof are excluded. In some embodiments, the composition excludes mineral oil, silicone oil, petroleum based oil, or a combination thereof.

In accordance with the various embodiments, oil may be present from about 0.01% to about 20%. One of ordinary skill in the art, however, will appreciate that other ranges are within the scope of the invention.

In some embodiments, the composition may include at least one wax. In some particular embodiments, the at least one wax is selected from the group consisting of *Copernicia cerifera* (Carnauba) Wax, candelilla wax, sunflower wax and combinations thereof.

In some embodiments, the amount of wax, when present in the composition may be from about 0.05% to about 5%, or from about 0.05% to about 1%, or 0.1% or any suitable combination, sub-combination, range, or sub-range thereof by weight, based on the weight of the composition. One of ordinary skill in the art, however, will appreciate that other ranges are within the scope of the invention.

In accordance with the various embodiments, the amount of fatty compound present in the composition can range from about 0.01% to about 40%, or from about 0.5% to about 30%, or from about 1% to about 25%, or from about 2% to about 15%, or from about 3% to about 5%, % or any suitable combination, sub-combination, range, or sub-range thereof by weight, based on the weight of the composition. One of ordinary skill in the art, however, will appreciate that other ranges are within the scope of the invention. In some embodiments, two or more fatty compounds are present. And, in some embodiments, one or more fatty compounds are present wherein at least one is an oxidation resistant fatty compound.

Thus, any one of or a combination of fatty compounds, if present, may be present, by weight, based on the total weight of the composition, or from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, to about 60 weight percent, including increments and ranges therein and there between.

Plasticizers

In accordance with the disclosure, one more plasticizers is present in the composition.

Generally, plasticizers tend to modify mechanical properties of a composition by reducing the Glass Transition Temperature (Tg) and increasing the softness and flexibility of films. In some embodiments, suitable plasticizers have a boiling point measured at ambient pressure of less than or equal to 285° C., in some embodiments less than or equal to 270° C., and in some embodiments less than or equal to 250° C. In the present specification, the boiling point values are to be considered accurate to +2° C. owing to the uncertainties of boiling point measurement. Useful plasticizers include glycerin, lecithin, polysorbates, dimethicone copolyol, glycols, citrate esters, dimethicone, and other similar ingredients disclosed in the International Cosmetic Ingredient Dictionary and Handbook Vol. 4 (9th ed. 2002), more particularly the plasticizers disclosed on page 2927.

In some embodiments the composition comprise glycerin as the plasticizer.

Examples of suitable plasticizers include, but are not limited to glycols and their ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, glycerin, diisobutyl adipate, the ester of tertbutyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, ethyl tosylamide and mixtures thereof.

In accordance with the various embodiments, the amount of each plasticizer, can range from about 0.1% to about 35%, or from about 0.5% to about 25%, or from about 1% to about 20%, or from about 2% to about 10%, or about 5%, or any suitable combination, sub-combination, range, or sub-range thereof by weight, based on the weight of the cleansing composition. One of ordinary skill in the art, however, will appreciate that other ranges are within the scope of the invention.

Thus, each plasticizer or combination thereof is present, by weight, based on the total weight of the composition, from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 to about 35 weight percent, including increments and ranges therein and there between.

Metal Salt

In some embodiments, the composition expressly excludes metal salts. In some embodiments, the composition expressly excludes or essentially free from any one or more of metal salts selected from calcium chloride, a manganese salt of pyrrolidone carboxylic acid, manganese gluconate, manganese sulfate, manganese chloride, a copper salt of pyrrolidone carboxylic acid, copper gluconate, copper sulfate, copper chloride, a zinc salt of pyrrolidone carboxylic acid, zinc gluconate, zinc sulfate, zinc chloride, or combinations thereof.

In accordance with the various embodiments, the composition includes at least one metal salt. Suitable metal salts include, but are not limited to, calcium chloride, a manganese salt of pyrrolidone carboxylic acid, manganese gluconate, manganese sulfate, manganese chloride, a copper salt of pyrrolidone carboxylic acid, copper gluconate, copper sulfate, copper chloride, a zinc salt of pyrrolidone carboxylic acid, zinc gluconate, zinc sulfate, zinc chloride, or combinations thereof.

In some particular embodiments, the metal salt is calcium chloride.

In accordance with the various embodiments, the amount of the at least one metal salt present in the composition can range from about 0.01% to about 1%, or from about 0.02% to about 0.5%, or from about 0.025% to about 0.1%, or from about 0.03% to about 0.05%, or about 0.035%, or any suitable combination, sub-combination, range, or sub-range thereof by weight, based on the weight of the skin treatment system. One of ordinary skill in the art, however, will appreciate that other ranges are within the scope of the invention.

Thus, any one of or a metal salts may be present, by weight, based on the total weight of the composition, or from about from about 0.01, 0.015, 0.02, 0.025, 0.03, 0.035, 0.04, 0.045, 0.05, 0.055, 0.06, 0.056, 0.07, 0.075, 0.08, 0.085, 0.09, 0.095, 0.10, 0.20, 0.30, 0.40, 0.50, 0.60, 0.70, 0.80, 0.90, to about 1.0 weight percent, including increments and ranges therein and there between.

Surfactant

In accordance with the various embodiments, the composition may include one or more surfactants.

In some embodiments the one or more surfactants are selected from low HLB and high HLB nonionic surfactants. In some embodiments one or more surfactants are sorbitol-based non-ionic surfactants.

In some embodiments the one or more surfactants are selected from sorbitan isostearate, polysorbate 60, stearic acid, cetearyl alcohol, polysorbate 20, glyceryl stearate (and) peg-100 stearate, cetearyl alcohol (and) ceteareth-20, glyceryl stearate, sorbitan stearate, and combinations thereof.

In some particular embodiments, the composition includes a blend of surfactants comprising sorbitan isostearate and polysorbate 60. In some exemplified embodiments, the composition includes a blend of surfactants comprising sorbitan isostearate (present at ~0.0275%) and polysorbate 60 (present at ~0.0275%).

In accordance with the various embodiments, the amount of surfactant present in the composition may be from about 0.01% to about 20%, or from about 0.05% to about 15%, or from about 0.4% to about 10%, or from about 0.5% to about 5%, or any suitable combination, sub-combination, range, or sub-range thereof by weight, based on the weight of the composition. One of ordinary skill in the art, however, will appreciate that other ranges are within the scope of the invention.

In some embodiments, surfactants selected are sulfate free. In some particular embodiments, the blend of surfactants comprises two or more surfactants that are sulfate-free. The term "sulfate-free" as used herein means that sulfate has not been added as a component. In some embodiments, a composition is devoid of sulfate. Those of skill in the art will appreciate that sulfate may be present in a composition via its presence in one or more of the formulation components; thus, in some embodiments a composition may be "essentially sulfate-free" wherein sulfate is present at a concentration that does not exceed 5% by weight, and in some instances is present not more than 3% by weight, and in some instances is present not more than 1% by weight, based on the weight of the cleansing composition. Thus, the term "sulfate-free" means that the surfactant does not include sulfate. Some examples of excluded sulfate surfactants include any one or more of alkyl sulfates, alkyl ether sulfates, alkylamido ether sulfates, alkylaryl polyether sulfates, monoglyceride sulfates, derivatives thereof, or combinations thereof.

Thus, each one of the surfactants, alone or in combination, is present in an amount by weight, based on the total weight of the moisturizing peel cream, from about 0.01, 0.015, 0.02, 0.025, 0.03, 0.035, 0.04, 0.045, 0.05, 0.055, 0.06, 0.056, 0.07, 0.075, 0.08, 0.085, 0.09, 0.095, 0.10, 0.20, 0.30, 0.40, 0.50, 0.60, 0.70, 0.80, 0.90, 1, 2, 3, 4, 5, 6, 7, 8, 9, 10, 11, 12, 13, 14, 15, 16, 17, 18, 19, to about 20 weight percent, including increments and ranges therein and there between.

Polymers

In accordance with the disclosure, the composition may include at least one cosmetically acceptable polymer. In some embodiments, the polymer has a glass transition ($T_g$) that is in the range from about −70° C. to about −30° C. In particular, the composition may include at least one suitable polymer for aiding in emulsification of the composition in the presence of at least one emollient oil.

In some embodiments, wherein the composition lacks emollient oil, such an oil-free system (e.g., serum or gel), the polymer can be excluded. In some particular embodiments, the composition includes hydroxyethyl acrylate/sodium acryloyldimethyl taurate copolymer, in particular when the composition is in the form of an oil in water emulsion as exemplified herein wherein an emollient oil is present. In some embodiments, the least one cosmetically acceptable polymer is selected from the group consisting of natural and synthetic polymers including crosspolymers, gums, taurate based polymers, carbomers, polyacrylates, and combinations thereof.

In some embodiments, the at least one cosmetically acceptable polymer is selected from hydroxyethyl acrylate/sodium acryloyldimethyl taurate copolymer, acrylamide/sodium acryloyldimethyltaurate copolymer, carbomer, ammonium acryloyldimethyltaurate/steareth-25 methacrylate crosspolymer, acrylates/beheneth-25 methacrylate copolymer, acrylates/C10-30 alkyl acrylate crosspolymer, ammonium polyacryloyldimethyl taurate, sodium polyacrylate, polyacrylate crosspolymer-6, sclerotium gum, xanthan gum, cellulose gum, locust bean gum, carrageenan, gellan, xanthan gum and combinations thereof.

In some embodiments, any one of the least one cosmetically acceptable polymer is present in a range from about 0.4% to about 3%, by weight, based on the total weight of the composition. In some embodiments, the total amount of the cosmetically acceptable polymer present in the composition is not more than about 3%, total, by weight, based on the total weight of the composition. In some embodiments, the total amount of polymer is at least about 0.4%, or at least about 0.5%, or at least about 0.6%, or at least about 0.8%, or at least about 1%, or at least about 1.2%, or at least about 1.5%.

In some embodiments, the total amount of cosmetically acceptable polymer present in the composition is in an amount from about 0.3% to about 3%, or from about 0.5% to about 2.5%, %, or from about 0.5% to about 2%, or from about 0.6% to about 1.5%, or any suitable combination, sub-combination, range, or sub-range thereof by weight, based on the weight of the composition. One of ordinary skill in the art, however, will appreciate that other ranges are within the scope of the invention.

Thus, each one polymer or combination of polymers in the composition is present by weight, based on the total weight of the composition, as disclosed above from about 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, to about 3.0 percent, including increments and ranges therein and there between.

Water

The compositions comprise from about 1% to about 80% by weight of water, with respect to the total weight of the composition. In some embodiments, the amount of water in the composition can range from about 5% to about 75%, or from about 10% to about 70%, or any suitable combination, sub-combination, range, or sub-range thereof by weight, based on the weight of the composition.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the composition, in particular the water phase of the composition, may be adjusted prior to combining the oil phase with the water phase to avoid the practical difficulty with measuring pH in an internal water phase of the water-in-oil emulsion. In various embodiments, the pH is a physiologically acceptable pH. In some embodiments, the pH of the water phase prior to emulsification can be adjusted with pH adjusters to a pH in a range from about 5 to about 7 by addition of a base (organic or inorganic) to the composition, for example sodium hydroxide, ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Thus, water may be present by weight, based on the total weight of the composition, or from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, to about 70, 71, 72, 73,74, 75, 76, 77, 78, 79 to about 80 weight percent, including increments and ranges therein and there between.

Solvent

In accordance with the disclosure, one or more solvent may be present in the composition. The solvent present in the cosmetic composition, according to the disclosure, includes, but is not limited to, water, alcohol, propylene glycol, or combinations thereof. In some embodiments, the solvent includes only water. In other embodiments, the solvent includes water and one or more other solvents. Although these solvents are given as an example, it will be appreciated that other solvents compatible with cosmetic applications known in the art may be used. In some particular embodiments, solvents include water.

In accordance with some embodiments, the composition may include one or more water-soluble solvent. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90% in water under these conditions. Non-limiting examples of water-soluble solvents include, for example, glycerin, alcohols (for example, C1-C30, C1-C15, C1-C10, or C1-C4 alcohols), polyols, glycols, and combinations thereof.

Examples of water-soluble solvents, ethylene glycol, propylene glycol, butylene glycol, hexylene glycol, propane diol, and glycerin. The organic solvents can be volatile or non-volatile compounds. Further non-limiting examples of water-soluble solvents include alkanols (polyhydric alcohols such as glycols and polyols) such as glycerin, 1,2,6-hexantriol, trimethylolpropane, ethylene glycol, propylene glycol, diethylene glycol, butylene glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-isopropyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and combinations thereof.

In accordance with the various embodiments, the total amount of the water-soluble solvent, when present, is present from about 0.5% to about 70%, or from about 1% to about 60%, or from about 5% to about 50%, or from about 10% to about 40%, or from about 20% to about 30% or any suitable combination, sub-combination, range, or sub-range thereof by weight, based on the weight of the skin care composition. One of ordinary skill in the art, however, will appreciate that other ranges are within the scope of the invention.

It will be appreciated by a skilled artisan that any solvents are present only to the extent and in amounts that do not materially adversely affect the basic and novel characteristic(s) of the claimed disclosure.

Thus, one or a combination of solvents may be present, by weight, based on the total weight of the composition from about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, to about 70 weight percent, including increments and ranges therein and there between.

Humectant

In accordance with the disclosure, one or more humectants may be present in the composition. In some embodiments the humectant may serve as a plasticizer. In some embodiments, the humectant may comprise one or more of glycerin, glycerol, glycols, such as, caprylyl glycol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers, such as, monopropylene, dipropylene and tripropylene glycol alkyl(C1-C4) ethers, squalane, triacetin, sugars, such as, glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some particular embodiments, a composition according to the disclosure may include at least one humectant that is a sugar, for example a mono-, di- or saccharide, in some specific examples, a sugar selected from sucrose, lactose, maltose, glucose, fructose, dextrose, galactose, xylitol, maltitol, sorbitol, inositol or combinations thereof.

In accordance with the various embodiments, the amount of humectant present in the composition can range from about 1% to about 20%, or from about 1% to about 15%, or from about 1% to about 10%, or about 5%, or any suitable combination, sub-combination, range, or sub-range thereof by weight, based on the weight of the skin care composition. One of ordinary skill in the art, however, will appreciate that other ranges are within the scope of the invention.

Thus, any one of or a combination of humectant, when present, may be present, by weight, based on the total weight of the composition, is from about 1, 2, 3, 4, 5, 6, 7, 8, 9, 10, 11, 12, 13, 14, 15, 16, 17, 18, 19 to about 20 weight percent, including increments and ranges therein and there between.

It will be appreciated by a skilled artisan that any humectants are present only to the extent and in amounts that do not materially adversely affect the basic and novel characteristic(s) of the claimed disclosure.

Optional Components

In some embodiments, there may be one or more actives present in the cosmetic composition, according to the disclosure, the additive selected from, for example, preservatives/anti-microbials (for example, chlorphenesin, salicylic acid, phenoxyethanol, potassium sorbate, and caprylyl glycol); actives (for example, hydroxyacetophenone); vitamins (for example, vitamin A, beta carotene, tocopherol/vitamin E, panthenol, retinol, resveratrol, vitamin C, niacinamide, derivatives thereof, and combinations thereof); hyaluronic acid is in the form of hydrolyzed hyaluronic acid. In some embodiments, the hyaluronic acid is in the form of sodium hyaluronate; coloring materials/pigments; essential oils; antioxidants (phenolic compounds, such as chalcones, flavones, flavanones, flavanols, flavonols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, and phenolic terpenes, resveratrol, curcumin, pinoresinol, ferulic acid, hydroxytyrosol, cinnamic acid, caffeic acid, p-coumaric acid, baicalin (*Scutellaria baicalensis* root extract), pine bark extract (*Pinus pinaster* bark/bud extract), ellagic acid); vitamins and vitamin derivatives, such as calcium pantothenate, tocopherol and ascorbic acid; hydroxy acids; citric acid, sodium citrate, sodium chloride; neutralizing, chelating or pH-adjusting agents (for example, triethylamine (TEA), trisodium ethylenediamine disuccinate, EDTA, and sodium hydroxide); powders, fragrances, dyes, pigments; organic or mineral UV filters; and combinations thereof.

In some particular embodiments, a composition according to the disclosure may include one or more of sucrose, sodium hydroxide, citric acid, phenoxyethanol, tocopherol, escin, dipotassium glycyrrhizate, and combinations thereof.

In some exemplified embodiments, a composition according to the disclosure may include one or more of sucrose (present at ~1.4%), sodium hydroxide (present at ~1.0%), citric acid (present at ~0.00003%), phenoxyethanol (present at ~0.50%), tocopherol (present at ~0.0015%), escin (present at ~0.30%), dipotassium glycyrrhizate (present at ~0.30%), and combinations thereof.

Although the aforementioned optional components are given as an example, it will be appreciated that other optional components compatible with cosmetic applications known in the art may be used.

In accordance with the various embodiments, the amount of one or more actives and additives, alone or in combination, when present in the composition according to the disclosure can be present in a range from about 0.0001% to about 20%, and in some embodiments, from about 0.005% to about 0.01%, and in some embodiments, from about 0.01% to about 0.1%, and in some embodiments, from about 0.15% to about 5%, and in some embodiments, from about 0.40% to about 4%, and in some embodiments, from about 0.5% to about 2.5%, and in some embodiments, from about 0.1% to about 0.5% and in some embodiments, from about 1% to about 2%, or any suitable combination, sub-combination, range, or sub-range thereof by weight, based on the total weight of the composition. One of ordinary skill in the art, however, will appreciate that other ranges are within the scope of the invention.

Thus, any one or a combination of actives and additives may be present, each one or the combination present from about 0.0001, 0.0005, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 percent, by weight, including increments and ranges therein and there between.

The examples below according to the invention are given by way of illustration and without a limiting nature. The names are the chemical name or the INCI name. The amounts are given therein as % by weight, unless otherwise mentioned.

Systems and Articles of Manufacture

In accordance with the various embodiments, the composition may be provided in an applicator or in a separate package provided with an applicator to enable precise and controlled application to skin other than by contacting the composition to the target skin with fingers.

It will be appreciated that in the various embodiments of packaging, the composition may be contained within an applicator container for application using a brush, roller ball, sprayer, pad or other surface. In some embodiments, the composition may be packaged separate from the applicator in a tube, packet, bottle or jar together with the applicator which is used at the time the composition is intended to be applied to keratinous tissue, at which time they the composition is applied to or dispensed into the applicator.

EXAMPLES

The examples below according to the invention are given by way of illustration and without a limiting nature. The names are the chemical name or the INCI name. Compositions and systems as described in the representative embodiments herein are selected from commercially available materials, including, as shown in the exemplified embodiments herein below.

Example 1: Raw Materials

TABLE 1

Raw Materials

| RM INGREDIENT/SOURCE | PERCENT ACTIVE (IF <100%) |
|---|---|
| LM PECTIN Commercial Reference: Unipectine of 600 C SB; Manufacturer: Cargill | 80% |
| HYDROXYETHYL ACRYLATE/SODIUM ACRYLOYLDIMETHYL TAURATE COPOLYMER Commercial Reference: Sepinov EMT 10 Manufacturer: SEPPIC | 89% active |

The inventive composition as exemplified herein includes the foregoing raw materials wherein the active constituents of the raw materials are listed as discrete ingredients; the amounts of active ingredients are given for the exemplified compositions as % by weight of the active ingredients based on the weight of the entire composition, not as amounts of raw materials, except as may be expressly stated.

Example 2: Inventive Compositions and Systems

An exemplary embodiment of the inventive composition is shown in Table 2.

TABLE 2

Inventive Composition

| INCI US | INV 1 |
|---|---|
| PECTIN | 5-6 |
| SILICA | 2.5-3.5 |
| GLYCERIN | 4-6 |
| CALCIUM CHLORIDE | 0.025-0.04 |
| HYDROXYETHYL ACRYLATE/SODIUM ACRYLOYLDIMETHYL TAURATE COPOLYMER | 0.4-0.5 |
| BUTYROSPERMUM PARKII (SHEA) BUTTER | 2.5-3.5 |
| ASTROCARYUM MURUMURU SEED BUTTER | 2.5-3.5 |
| SUCROSE | 0.8-1.6 |
| ACTIVES/OTHER ADDITIVES (TOCOPHEROL, ESCIN, DIPOTASSIUM GLYCYRRHIZATE, PHENOXYETHANOL, SODIUM HYDROXIDE, CITRIC ACID) | ~2.1 |
| SURFACTANTS (POLYSORBATE 60, SORBITAN ISOSTEARATE) | ~0.05-0.06 |
| WATER | QS |

Example 3: In Vivo Assessment of an O/W Prototype Including Pectin/SiO$_2$ on a Volunteer's Face An embodiment of the inventive composition according to the disclosure was evaluated in an oil and water formulation INV 1. The composition was applied to the wearers face and tightening effect on wrinkles and bags in the eye area were assessed a timer intervals from immediately prior to application to 7 hours post application; results are shown in Table 3 and in FIG. 3 which presents photographic images of a test subject demonstrating in vivo evaluation of a prototype formula including pectin/SiO$_2$. As shown in these results, the tested embodiment of the inventive composition demonstrates superb wrinkle smoothing, tightening and long-lasting efficacy over a period of at least 7 hours.

TABLE 3

In vivo test results

| Time relative to Application | Visible Effect | Comfort, Aesthetics of Firming Film |
|---|---|---|
| Before | Evident bags and lines beneath eyes | |
| 10 min post appl. | Bags and lines eliminated | Flexible without folding or pinching; no flaking or cracking |
| 60 min post appl. | Results from 10 min sustained | Results from 10 min sustained |
| 3 hr post appl. | Results from 10 min sustained | Results from 10 min sustained |
| 5 hr post appl. | Results from 10 min sustained | Results from 10 min sustained |
| 7 hr post appl. | Results from 10 min sustained | Results from 10 min sustained |

As demonstrated in the in vivo study, the inventive composition including the firming system provided in a direct oil in water emulsion, dispersion or emulsion gel format, demonstrated superb skin tightening and antiaging efficacy almost immediately with a long lasting effect that was maintained up to at least 7 hours post application. The skin care composition including the firming system that includes the novel combination of pectin and silica together with emollient oil and plasticizer glycerin provides cohesion of the firming film after drying on skin and desirable adhesion, elasticity and compliance to offer balanced benefits of efficacy to tighten skin and reduce or eliminate wrinkles and bags with immediate and lasting effect without compromising skin comfort and aesthetics.

Figure 3:
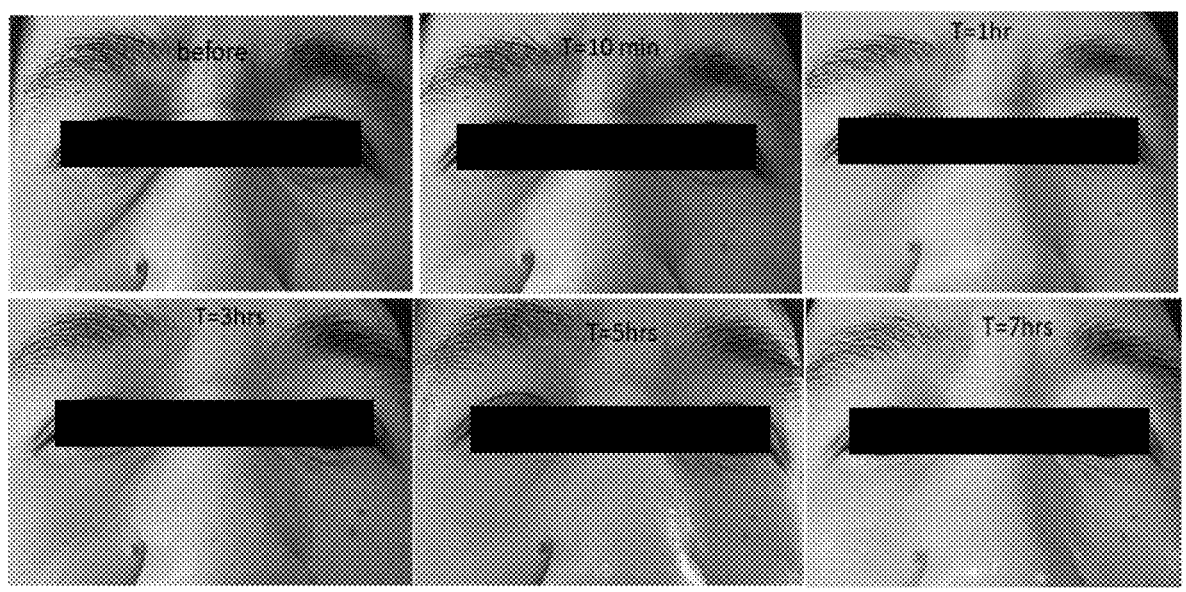
FIG. 3 demonstrates film property in vivo test results, in accordance with an embodiment of the disclosure.

Example 4: In Vitro Assessment of Film Cohesion/Adhesion: Blend of Pectin and Polymer In vitro evaluation of different samples on nitrile substrate were evaluated for cohesion and adhesion, wherein, after film drying, the results as shown in FIG. 3 demonstrate the superb internal stress arising from the combination of pectin and silica.

Figure 4:
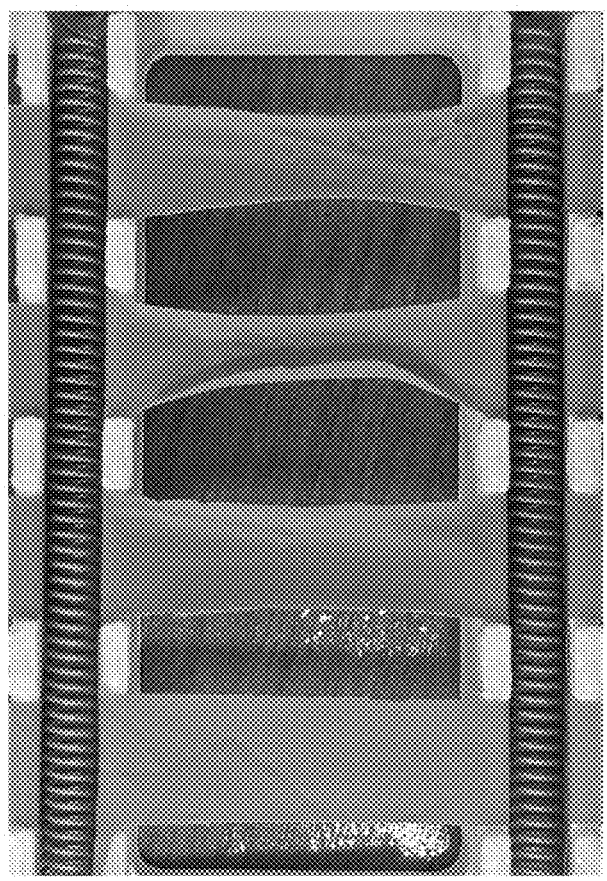
FIG. 4 demonstrates additional film property in vitro test results, in accordance with an embodiment of the disclosure.

The experiment was run with test films arranged as shown in Table 4. Results are reflected in FIG. 4.

TABLE 4

| In vitro testing of varied combinations of pectin with polymer |
|---|
| Samples |
| Aqueous dispersion of 5% w/w pectin and 2% w/w $Na_2SiO_3$ |
| Aqueous dispersion of 5% w/w pectin and 2% w/w $SiO_2$ |
| Aqueous dispersion of 5% w/w pectin |
| Blank substrate |

Figure 5:
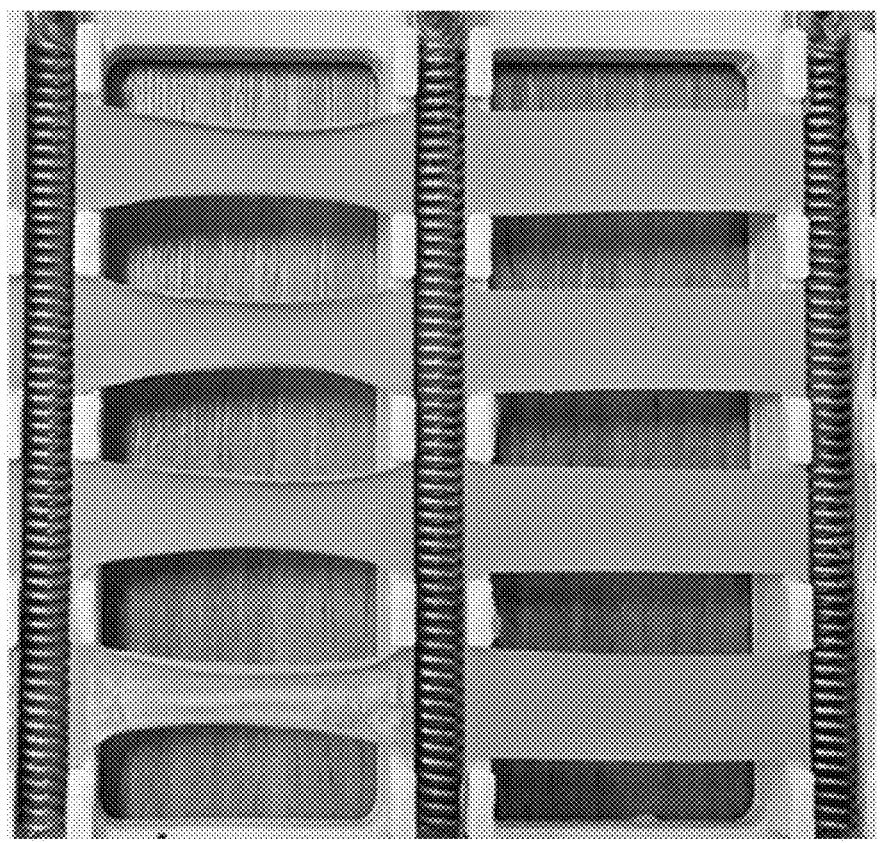
FIG. 5 demonstrates additional film property in vitro test results, in accordance with an embodiment of the disclosure.

Example 5: In Vitro Assessment of Film Cohesion/Adhesion: Blend of Pectin and Polymer In vitro evaluation of different samples on nitrile substrate were evaluated for cohesion and adhesion, wherein, after film drying, the results as shown in FIG. 5 demonstrate the superb internal stress and non-flaking properties arising from the inventive combination of pectin and silica (prototypes 1, 2 and 3).

TABLE 5

Inventive prototype 1
PROTOTYPE 1

| Ingredient | % Concentration |
|---|---|
| Water/Aqua | 72.4% |
| Sodium Hydroxide | 1.1% |
| Pectin | 7% |
| Silica | 3% |
| Sodium Hyaluronate | 0.5% |
| Glycerin | 8.5% |
| Caprylyl Glycol | 0.5% |
| Hydroxyethyl Acrylate/Sodium Acryloyldimethyl Taurate Copolymer | 1.5% |
| Butyrospermum Parkii (Shea) Butter/Butyrospermum Parkii Butter | 2% |
| Astrocaryum Murumuru Seed Butter | 3% |
| Phenoxyethanol | 0.5% |

TABLE 6

Inventive prototype 2
PROTOTYPE 2

| Ingredient | % Concentration |
|---|---|
| Water/Aqua | 74.9% |
| Sodium Hydroxide | 1.1% |
| Pectin | 7% |
| Silica | 3% |
| Sodium Hyaluronate | 0.5% |
| Glycerin | 6% |
| Caprylyl Glycol | 0.5% |
| Hydroxyethyl Acrylate/Sodium Acryloyldimethyl Taurate Copolymer | 1.5% |
| Butyrospermum Parkii (Shea) Butter/Butyrospermum Parkii Butter | 2% |
| Astrocaryum Murumuru Seed Butter | 3% |
| Phenoxyethanol | 0.5% |

TABLE 7

Inventive prototype 3
PROTOTYPE 3

| Ingredient | % Concentration |
|---|---|
| Water/Aqua | 73.9% |
| Sodium Hydroxide | 1.1% |
| Pectin | 7% |
| Silica | 3% |
| Sodium Hyaluronate | 0.5% |
| Glycerin | 6% |
| Caprylyl Glycol | 0.5% |
| Hydroxyethyl Acrylate/Sodium Acryloyldimethyl Taurate Copolymer | 1.5% |
| Butyrospermum Parkii (Shea) Butter/Butyrospermum Parkii Butter | 3% |
| Astrocaryum Murumuru Seed Butter | 3% |
| Phenoxyethanol | 0.5% |

Comparative Ingredients

Water/Aqua/Eau, Glycerin, Butylene Glycol, Sodium Silicate, Sodium Magnesium Fluorosilicate, Magnesium Aluminum Silicate, Dipeptide-2, Palmitoyl Tetrapeptide-7, *Argania spinosa* Kernel Extract, Hesperidin Methyl Chalcone, Hydrolyzed Lupine Protein, Sodium Cocoyl Glutamate, *Medicago sativa* (Alfalfa) Seed Extract, Tocopheryl Acetate, Ascorbic Acid, Panthenol, Sodium Citrate, Carbomer, *Foeniculum vulgare* (Fennel) Seed Extract, *Symphytum officinale* Leaf Extract, Chlorhexidine Digluconate, Ethylhexylglycerin, Steareth-20, Carrageenan, Sodium Phytate, Potassium Sorbate, Sodium Benzoate, Citric Acid, Phenoxyethanol, The experiment was run with test films arranged as shown in Table 8. Results are reflected in FIG. 5.

TABLE 8

| In vitro testing of varied Inventive prototypes vs blank controls (water) | |
|---|---|
| Prototype 1 | Blank |
| Prototype 2 | Blank |
| Prototype 3 | Blank |
| Comparative | Blank |

The inventive compositions were compared with a commercial benchmark, Peter Thomas Roth—Instant Eye Firming™, and control (no applied composition). Referring now to FIG. 5, each of the blanks evidenced no noticeable curling of the test bands. Each of the inventive and the comparative demonstrated significant tightening and curling of approximately equal extent, however, the comparative was flaking and bubbled, evidencing brittleness, poor cohesion of the film and poor adhesion to the substrate.

Figure 6:
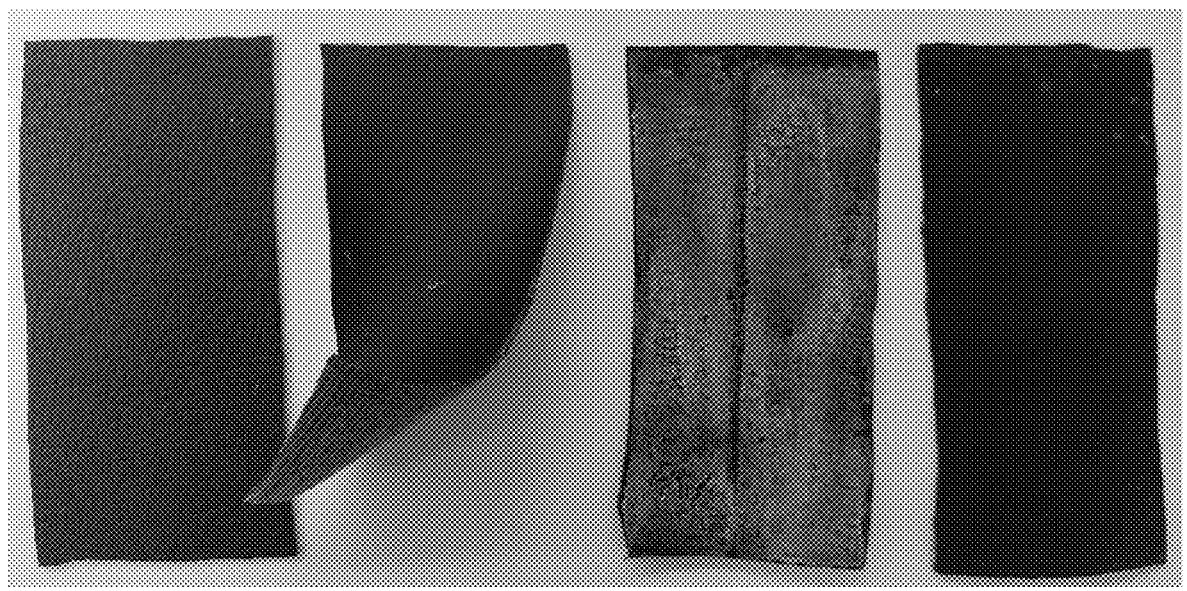
FIG. 6 demonstrates additional film property in vitro test results, in accordance with an embodiment of the disclosure.

Example 6: In Vitro Demonstration of Tightening and Flaking Properties of Various Sample Films on Protein Leather Substrate In vitro evaluation of different samples on leather substrate of Supplare (Miyoshi) were evaluated for cohesion and adhesion, wherein, after film drying, the results as shown in FIG. 6 demonstrate left to right: bare substrate, substrate with a prototype formula 2 film including pectin/$SiO_2$, substrate with film of Comparative and substrate with a common wrinkle smoothing face cream commercially available on market. As plainly shown in FIG. 6, the test results show that the firming system including pectin with one of silica microspheres and silicate produces films that provide tightening without significant flaking, lifting or bubbling, whereas the Comparative was flaking and bubbled, evidencing brittleness, poor cohesion of the film and poor adhesion to the substrate.

While illustrative embodiments have been illustrated and described, it will be appreciated that various changes can be made therein without departing from the spirit and scope of the invention.

The term "Cosmetically acceptable" means compatible with any keratinous substrate. For example, "cosmetically acceptable carrier" means a carrier that is compatible with any keratinous substrate.

The term "firming system" means and refers to the combination of pectin with powder, in some embodiments silica microspheres or silicates or both, to form a firming film that confers tightening to a substrate. In some examples, particularly for cosmetic applications according to the disclosure, the substrate is a keratinous substrate such as skin or hair.

The term "firming film" means and refers to a film formed according to the disclosure having an essentially uninterrupted surface along the length and breadth of the film as applied to a substrate, for example, a keratinous substrate such as skin. In various embodiments, the film has a thickness that may be constant or may vary across a surface of a substrate on which it is spread, such as but not limited to application on all or portions of skin, such as but not limited to facial skin, or hair such as but not limited to eyelashes, eyebrows and on the head. In some embodiments, the thickness of the film does not vary by more than 5%. The film may include skin actives that may confer additional benefits including moisturizing, lightening and brightening. The firming film demonstrates cohesion and good adherence to the substrate with little or no bubbling and without flaking, peeling or cracking.

The terms "tighten" and "tightening" means that the firming film contracts in a manner that the substrate, such as skin or hair, is tensed and modestly tightened as compared to the skin without the film such that the film reduces the visual appearance of wrinkles in the skin.

The terms "Exclude," "Free" and "Essentially Free" mean that no reliably measurable excluded material, for example, no amount greater than about 5%, by weight, based on the total weight of the composition, of any excluded material as described herein, is present in the composition. The terms "Exclude," "Free" and "Essentially Free" mean that, while it is preferred that no excluded material is present in the composition, it is possible to have very small amounts of the excluded material in the composition of the invention, provided that these amounts do not materially affect the advantageous properties of the composition. In particular, the terms "Exclude," "Free" and "Essentially Free" mean that material can be present in the composition at an amount of less than 5%, or less than 4%, or less than 3%, or less than 2%, or less than 1%, or less than 0.1% by weight, based on the total weight of the composition. In accordance with the various embodiments, it is contemplated that some or all of following ingredients would be excluded from the composition according to the invention: powders comprising Nylon-12, polymethyl methacrylate, polyethylene beads, and powders which are considered microplastics; lactic acid, glycolic acid, tartaric acid, mandelic acid, citric acid, salicylic acid and derivatives thereof (including 5-n-octanoyl-salicylic acid, salicylate, sodium salicylate, and willow extract), capryloyl salicylic acid, beta hydroxybutanoic acid, propionic acid, beta-hydroxy beata-methylbutyric acid, carnitine tropic acid, and trethocanic acid; alkyl polyglucosides selected from the group consisting of decyl glucoside, lauryl glucoside, octyl glucoside, coco glucoside, caprylyl/capryl glucoside, and sodium lauryl glucose carboxylate, and combinations thereof; surfactants with a C10-C20 fatty alcohol or acid hydrophobe condensed with from about 2 to about 100 moles of ethylene oxide or propylene oxide per mole of hydrophobe; C2-C10 alkyl phenols condensed with from 2 to 20 moles of alkylene oxide; mono- and di-fatty acid esters of ethylene glycol; fatty acid monoglyceride; sorbitan; mono- and di-C8-C20 fatty acids; polyoxyethylene sorbitan; alkyl polyglycosides and saccharide fatty amides (e.g. methyl gluconamides); alkyl ether sulfate and sulfonates; alkyl sulfates and sulfonates; alkylbenzene sulfonates; alkyl and dialkyl sulfosuccinates; C8-C20 acyl isethionates; C8-C20 alkyl ether phosphates; alkylethercarboxylate, PEG-100 Stearate; PEG-20 Stearate and other esters of Poly(Ethylene Glycol); Sucrose Stearate and other emulsifiers based on sugar esters; Glyceryl Stearate and other glycerol esters; Disodium Ethylene Dicocamide PEG-15 Disulfate; Sodium Steroyl Glutamate and other fatty amides; Steareth-100 and other fatty ethers, cationic surfactants, and other cationic compounds, silicones, such as silicone polymers, silicone elastomers, and silicone oils, for example selected from dimethicone, cyclopentasiloxane, cyclohexasiloxane, and combinations thereof, phthalates, parabens, sulfates, polyquaternium, microplastics, synthetic dyes, gelling agents, and combinations thereof.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising," "consisting essentially of" and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of." Further, It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

Other than in the operating examples, or where otherwise indicated, all numbers expressing quantities of ingredients and/or reaction conditions are to be understood as being modified in all instances by the term "about," meaning within 10% of the indicated number (e.g., "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to about 10%, such as 2% to about 8%, such as 3% to about 5%," is intended to encompass ranges of "1% to about 8%," "1% to about 5%," "2% to about 10%," and so on. All numbers, amounts, ranges, etc., are intended to be modified by the term "about," whether or not so expressly stated. Similarly, a range given of "about 1% to about 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cosmetic composition, comprising:
   a firming system that includes:
      from about 0.5-about 10% of pectin;
      at least one powder comprising about 0.1 to about 10% of silica microspheres; water;
      at least one fatty compound comprising from about 4% to about 8% of plant butters; and
      at least one plasticizer;
   wherein all amounts are present by weight, based on the weight of the composition,
   wherein the firming system is spreadable and wherein upon drying the firming system forms a firming film that exhibits cohesion and adhesion when applied to a substrate, and
   wherein the firming system is entirely free of polysaccharides other than pectin.

2. A cosmetic system, comprising:
   an applicator; and
   a firming system that includes:
      pectin;
      at least one powder;
      water; and
      at least one plasticizer; and
   a cosmetic carrier system for a cosmetic product selected from the group consisting of a skin anti-aging treatment and a makeup,
   wherein the firming system is spreadable and wherein upon drying the firming system forms a firming film that exhibits cohesion and adhesion when applied to a substrate, and
   wherein the firming system is entirely free of polysaccharides other than pectin.

3. The cosmetic system according to claim 2, wherein the applicator is selected from a roller surface of a rolling applicator, a bristle surface of a brush, a sprayer, a pad, a spatula, or combinations thereof.

4. The cosmetic system according to claim 2, wherein the composition is contained within the applicator, or wherein the cosmetic system comprises a container and wherein the composition is separately contained from the applicator.

5. The cosmetic system according to claim 2, wherein the firming system and cosmetic carrier system is in the form of liquidous or creamy emulsion comprising at least one fatty compound, or an oil free serum for application to skin to ameliorate the signs of aging.

6. The cosmetic system according to claim 2, wherein the firming system and cosmetic carrier system is in the form of viscous liquidous emulsion or suspension for application as a makeup to keratinous tissue selected from skin, lashes and hair to confer firming to the keratinous tissue.

* * * * *